United States Patent [19]

Löbmann et al.

[11] 4,338,296

[45] Jul. 6, 1982

[54] INFLUENZA VIRUS AND PROCESS OF PRODUCING A VACCINE THEREFROM

[75] Inventors: Michèle Löbmann, Bierges; Gérard Florent, Genval, both of Belgium

[73] Assignee: SmithKline-RIT, Belgium

[21] Appl. No.: 231,528

[22] Filed: Feb. 4, 1981

Related U.S. Application Data

[62] Division of Ser. No. 85,437, Oct. 16, 1979, Pat. No. 4,278,662.

[51] Int. Cl.³ .......................... A61K 39/12; C12N 7/00
[52] U.S. Cl. ...................... 424/89; 435/235; 435/236
[58] Field of Search ................. 424/89; 435/235, 236, 435/237

[56] References Cited

U.S. PATENT DOCUMENTS

3,991,179  11/1976  Beare .................................... 424/89
4,009,258  2/1977  Kilbourne ............................. 424/89

*Primary Examiner*—Sam Rosen
*Attorney, Agent, or Firm*—Janice E. Williams; Richard D. Foggio; Alan D. Lourie

[57] ABSTRACT

The invention relates to a novel influenza virus strain and to the influenza virus vaccine containing said strain.

The new strain, which is the CNCM N° I-099 strain, is prepared by recombination of the influenza A/PR/8/34 virus strain with the influenza A/California/10/78 (CNCM N° I-098) virus strain.

The vaccine is prepared by allowing the CNCM N° I-099 strain to grow in the allantoic cavity of fertile hen's eggs, harvesting and freeze-drying the yielded virus material.

The strain and the vaccine deriving therefrom are valuable for the immunization against influenza caused by influenza type A ($H_1N_1$) virus strains.

4 Claims, No Drawings

INFLUENZA VIRUS AND PROCESS OF PRODUCING A VACCINE THEREFROM

This is a divisional of application Ser. No. 085,437, filed Oct. 16, 1979, now U.S. Pat. No. 4,278,662.

The present invention relates to a novel attenuated influenza type A virus strain and to the live influenza vaccine for nasal administration containing it.

Up to now, different techniques have been employed for attenuating influenza virus in view of the preparation of live influenza virus vaccines.

One of these techniques comprises the recombination of a pathogenic strain with an antigenically distinct virus strain known to be attenuated for man followed by the isolation of an adequate attenuated recombinant.

An example of vaccine obtained by a process involving virus recombination and isolation of an adequate attenuated recombinant is given by the U.S. Pat. No. 3,953,592.

It is known that a particular problem for the immunization against influenza virus type A results from the fact that almost every year the serotype of the influenza type A virus strain spreading throughout the world appears to be somewhat different from the serotype of the previously observed strains. In order to be effective, a vaccinal antigen must be as close as possible to the antigen of the circulating strain and, consequently, a live attenuated influenza virus vaccine must be periodically updated.

Recombination between a recently isolated virulent circulating strain of influenza virus type A and a well known attenuated strain (e.g. the A/PR/8/34 influenza virus strain) constitutes a remarkable tool for rapid updating of influenza virus strains owing to the fact that, by recombination, the properties of one strain can be transferred to another strain within a very short period of time.

Nevertheless, recombination yields a wide variety of recombinants and only very few among them are suitable for vaccinal use. These latter ones indeed must show a number of characteristics such as serotype of the wild virus, attenuation, immunogenicity, non-transmissibility to persons in contact with vaccines, genetic stability, acceptable growth capacity and good storage stability.

To date, different markers have been developed for the selection of attenuated influenza type A virus strains which are then possible candidates for live vaccine production.

Examples of markers are the resistance of the strain to the inhibitors present in normal serum (as in U.S. Pat. No. 3,953,592) and the proportion of the genome donated by each parent and expressed as percentage of RNA-RNA hybridization (G. Florent in Developments in Biological Standardization Vol. 39 pp. 11–14, S. KARGER, Basel 1977).

We have now found a new and reliable biochemical marker of attenuation of an influenza virus recombinant for its administration to human beings. Contrary to the previously known markers, the present marker is based on the particular biochemical structure of the virus and is thus the expression of a structure/activity relationship. We have found indeed that a heterogenous constellation of the polymerase (P) genes of an influenza type A virus is a marker of sufficient attenuation for administration of the virus for vaccinal use to human beings.

To date, comparative studies have already been performed on the reassortment of genes by recombination of influenza viruses but no obvious correlation was found between the genome composition of the recombinants and their attenuation for man (J. S. Oxford et al., Nature, 273, 778–779, 1978).

Thus, according to this embodiment, the present invention relates to the production of an influenza type A virus strain by a process comprising recombination of an attenuated influenza virus strain (more particularly the A/PR/8/34 strain) with a recently isolated pathogenic strain (more particularly the influenza A/California/10/78 virus strain) and isolation of a recombinant having among other characteristics the serotype of the pathogenic parent strain and a heterogenous constellation of its polymerase (P) genes.

By recombination of the attenuated A/PR/8/34 ($H_0N_1$) influenza virus strain (which has a high growth capacity) with the pathogenic influenza A/California/10/78 ($H_1N_1$) virus strain, we have been able to isolate among the different resulting recombinants a novel influenza virus strain named RIT 4265 having the $H_1N_1$ serotype and valuable for the production of a live vaccine against the A/California/10/78 virus strain and the like, said novel attenuated influenza virus strain showing a heterogenous constellation of its polymerase (P) genes versus the polymerase (P) genes constellation of its A/PR/8/34 and A/California/10/78 parent strains.

The influenza A/California/10/78 virus strain is a wild strain isolated from a patient in California. It was received from the WHO Collaborating Center for Influenza, Atlanta, Ga., U.S.A. at the third passage in SPAFAS eggs (from SPAFAS INC., Storrs, Conn., U.S.A.). Its serotype is identical to the one of the influenza A/Brazil/11/78 ($H_1N_1$) prototype strain. The influenza A/California/10/78 strain has been deposited on Sept. 14, 1979 with the "Collection Nationale de Cultures de Microorganismes" (C.N.C.M.) of the "Institut Pasteur" in Paris under CNCM No. I-098.

The influenza RIT 4265 virus strain has been deposited with the same collection on Sept. 14, 1979 under CNCM No. I-099.

Thus, the present invention relates to the novel influenza A virus CNCM No. I-099 strain and to the live influenza virus vaccine comprising an effective dose of the influenza A virus CNCM No. I-099 strain and a pharmaceutical diluent for nasal administration.

The influenza A virus CNCM No. I-099 strain is a recombinant obtained by mixing aliquots of the A/PR/8/34 and CNCM No. I-098 strains, allowing the mixture to stay a few hours at 4° C., inoculating the mixture in the allantoic cavity of fertile hen's eggs, incubating the inoculated eggs, harvesting the viral material and cloning it by limiting dilution passages.

For preparing a vaccine according to the invention, the recombinant influenza A virus CNCM No. I-099 strain is allowed to grow in fertile eggs, more particularly in the allantoic cavity of fertile hen's eggs, according to any technique known to the art for the production of vaccines, for a period of time sufficient to permit production of a large amount of said virus, harvesting the resulting virus material and, if desired, adding thereto a stabilizer, such as for instance peptone, sucrose or any other one known to the art, distributing the mixture into glass vials to contain either single or multiple doses of vaccine and freeze-drying the preparation.

Preferably, an effective vaccine dosage unit contains at least $10^7 EID_{50}$ (50% egg infective dose) of virus.

The vaccine according to the invention is administered by the nasal route, eventually after extemporaneous reconstitution by addition of either water or any other pharmaceutical diluent or composition known to the art for the preparation of nasal preparations such as drops or spray.

For assuring the best vaccinal response, the vaccine may, if desired, be administered by inoculation of two successive dosage units at a one week interval.

The present invention is illustrated by the following examples wherein the indicated eggs all originate from specific pathogens free (SPF) flocks meeting the Specifications for the Production and Control of Avian Live Virus Vaccines established by the British Ministry of Agriculture, Fisheries and Food (1976).

These examples should not be construed as limiting the scope of the invention.

EXAMPLE 1

A 0.5 ml. aliquot of a reconstituted suspension of the lyophilized A/PR/8/34 influenza virus strain containing $10^{9.2}EID_{50}$ thereof per milliliter is mixed with a 0.5 ml. aliquot of allantoic liquid of fertile hen's eggs containing $10^{9.2}EID_{50}$ of the CNCM No. I-098 influenza virus strain per milliliter and the mixture is maintained at 4° C. for a few hours.

The mixture is then inoculated into the allantoic cavity of fertile hen's eggs which are incubated at 35° C. for 20 hours.

The progeny of this mixed culture is harvested, diluted to 1/10 (v/v) and mixed with the same volume of anti A/PR/8/34 hen's serum treated with receptor-destroying enzyme (RDE) and diluted 1/50 (v/v). After one hour, it is inoculated in the allantoic cavity of fertile hen's eggs which are then incubated for 24 hours at 35° C. Another passage is thereafter performed in the same conditions but for 48 hours.

The obtained virus is then cloned in the allantoic cavity of fertile hen's eggs by limiting dilution passages, a first passage being performed in the presence of treated and 1/100 (v/v) diluted anti A/PR/8/34 hen's serum, a second passage being performed without serum and two further passages being performed in the presence of normal guinea pig serum.

One so-isolated strain has been selected, characterized and assigned the RIT 4265 designation and deposited with the "Collection Nationale de Cultures de Microorganismes" (C.N.C.M.) of the "Institut Pasteur" in Paris on Sept. 14, 1979 under CNCM No. I-099.

EXAMPLE 2

Characterization of the influenza virus CNCM No. I-099 recombinant

The CNCM No. I-099 recombinant has been examined for its genotypic composition by using a technique based on the identification of the double stranded RNA formed by hybridization between the radioactive complementary RNA (c RNA) of the recombinant and the unlabelled virion RNA of the parent viruses (A. HAY et al. in Developments in Biological Standardization Vol. 39, pp. 15–24, S. KARGER, Basel 1977), as follows:

Complementary RNA (c RNA) and virion RNA (c RNA) preparation

Different chick embryo fibroblast monolayers are infected with A/PR/8/34, CNCM No. I-098 and CNCM No. I-099 virus strains respectively, using at least 2,000 hemagglutinin units of each virus. After a one hour incubation period at 36° C., $^3H$ labelled uridine is added in order to reach 100 $\mu$Ci per milliliter and, four hours after infection, the c RNA is extracted from the cytoplasmic extract as described by A. HAY in Virology 83, pp. 337–355, 1977.

Virion RNA is extracted from virus pellets using the phenol/SDS (sodium dodecyl sulfate) method described by C. Scholtissek in Biochem. et Biophys. Acta 179, pp. 389–397, 1979.

Hybridization and gel electrophoresis

Each c RNA preparation is divided into three aliquots. To the first one no v RNA is added while to the second and third aliquots are added v RNA (10 mcg) of A/PR/8/34 and CNCM No. I-098 strains respectively. Nine volumes of dimethyl sulfoxide are added and each mixture is incubated at 45° C. for 30 minutes. NaCl, Tris-HCl pH 7.5 and EDTA are added to give final concentrations of $3\times10^{-2}$ M, $10^{-2}$ M and $1.5\times10^{-3}$ M respectively, the concentrations of dimethyl sulfoxide is reduced to 63% and the solution is incubated at 37° C. for 12 hours.

The RNA is precipitated with two volumes of ethanol and redissolved in sodium acetate buffer pH 4.5 ($10^{-2}$ M), $ZnSO_4$ ($10^{-3}$ M). Nuclease S1, (2500 $\mu$/ml.) is added and, after incubation at 37° C. for four hours, the RNA is reprecipitated and dissolved in 7 M urea, EDTA ($5\times10^{-3}$ M), Trisacetate pH 7.8 ($2\times10^{-2}$ M). The double-stranded RNAs are separated by electrophoresis on 4% polyacylamide slab gels containing 7 M urea at 80 volts for 16 hours and detected by fluorography, giving for the CNCM No. I-099 recombinant the following genotypic composition.

| RNA fragment N° | Origin |
|---|---|
| 1 | A/PR/8/34 |
| 2 | I-098 |
| 3 | A/PR/8/34 |
| 4 | I-098 |
| 5 | A/PR/8/34 |
| 6 | I-098 |
| 7 | A/PR/8/34 |
| 8 | A/PR/8/34 |

EXAMPLE 3

Vaccine preparation

Influenza virus CNCM No. I-099 strain obtained at the end of the last passage of example 1, is used as inoculum for the production of vaccine seed batch production.

An aliquot of said CNCM No. I-099 strain obtained at the end of Example 1, is inoculated into the allantoic cavity of fertile hen's eggs which are then incubated at 35° C. for two to three days.

The allantoic fluids containing the CNCM No. I-099 strain are harvested, pooled and tested for sterility and innocuity and peptone is added thereto up to yielding a 5% (v/v) peptone concentration.

The virus suspension is distributed into 3 ml. vials in order to obtain dosage units (at least $10^7 EID_{50}$) of influenza virus and freeze-dried. The vials are then tightly stoppered.

For administration, the vaccine is reconstituted extemporaneously by addition of 0.5 ml. of a diluent which is for instance distilled water, normal saline or aqueous solution of sucrose (5% w/v) and the reconstituted vaccine is administered into the nostrils.

EXAMPLE 4

Vaccination with attenuated influenza virus vaccine, CNCM No. I-099 strain

Material and methods

Twenty two subjects from 16 to 48 year old (mean age: 25 years) having an HI antibody titre (i.e. determined by haemagglutination inhibition) equal to or inferior to 20, against CNCM No. I-099 strain, were selected for the clinical trial. To each subject a dosage unit of vaccine containing $10^{7.3} EID_{50}$ of the CNCM No. I-099 strain obtained at the end of example 3 and reconstituted just before administration in 0.5 ml. of a sterile 5% (w/v) sucrose aqueous solution was administered by the nasal route, each subject in supine position receiving 5 drops of vaccine in each nostril.

For the determination of seroconversion (which corresponds either to an HI antibody titre increase from <10 to ≧10 or, when the prevaccination HI antibody titre is ≧10 to a fourfold increase of the HI titre), blood samples were collected for the determination of HI antibody titre against the CNCM No. I-099 strain before vaccination and 21 days after vaccination. HI antibody titres were determined using A/Hong Kong/117/77, CNCM No. I-099 and A/Brazil/11/78 strains as antigens.

For 14 subjects having a HI titre ≦10, nasal washings were also performed one day before vaccination and on days 1, 2, 3, 5 and 7 after vaccination. A physical examination was performed on the day of vaccination (day 0). Check-lists for symptoms and body temperature recordings were filled daily by each vaccinee. Subjects were examined for the eventual symptoms such as: body temperature, stuffy nose, rhinorrhea, sore throat, hoarseness, headache, cough and expectoration.

RESULTS

1. Virus excretion

Nasal washings were performed in fourteen students having an HI titre <10 against CNCM No. I-099 (except No. 694 who had a titre of 10).

No haemagglutinating viruses were present in the nasal washings collected the day before vaccination.

The individual results of virus excretion on days 1, 2, 3, 5 and 7 are shown in Table I.

Two vaccinees excreted the vaccinal virus at high titre (>$10^3 EID_{50}$/0.2 ml.) on day 2 (No. 490) and on days 2 and 3 (No. 698). These titres decreased later and no virus was isolated on day 5 from No. 490 and on day 7 from No. 698.

Another vaccinee (No. 693) excreted the vaccinal virus from day 1 to 3 but at low titres.

Seven other vaccinees excreted the vaccinal virus on day 1 only (for No. 692 the virus was isolated after two passages in eggs) and one vaccinee (No. 695) excreted the virus on day 2 only.

TABLE I

VIRUS EXCRETION

Virus excretion (titre expressed in log $EID_{50}$/0.2 ml. of nasal washing)

| N° | Day 1 | 2 | 3 | 5 | 7 |
|---|---|---|---|---|---|
| 490 | NT | 4.5 | 2.5 | — | NT |
| 691 | — | — | — | — | — |
| 694 | — | — | — | — | NT |
| 698 | 1.6 | 3.25 | 3.0 | 0.25 | — |
| 703 | 1.0 | — | — | — | — |
| 705 | 0.5 | — | — | — | — |
| 707 | 0.5 | — | NT | NT | — |
| 712 | 0.2 | — | — | — | — |
| 713 | 1.3 | — | — | — | — |
| 715 | — | — | — | — | NT |
| 689 | 2.0 | — | — | — | — |
| 692 | + | — | — | — | — |
| 693 | 0.5 | 1.0 | 0.0 | — | — |
| 695 | — | 0.0 | — | — | — | wherein
— = negative
+ = positive at the second passage
NT = not tested.

2. Serology

Table II shows the individual HI titres before and 21 days after vaccination. Each sample was titrated against A/Hong Kong/117/77, CNCM No. I-099 and A/Brazil/11/78 (except No. 662, the serum of whom was not tested against A/Hong Kong/117/77 after vaccination).

Thirteen out of fourteen vaccinees who participated to the nasal washings had an HI titre ≦10 against CNCM No. I-099; among these 14 subjects, eleven seroconverted against the vaccinal antigen.

One vaccinee (No. 712) shed the vaccinal virus on day 1, seroconverted against the A/Brazil/11/78 but not against the A/Hong Kong/117/77 and the result against CNCM No. I-099 are at the limit of significance.

The two vaccinees who did not seroconvert against the three antigens (No. 703, 689) also shed the vaccinal virus indicating that all vaccinees were infected.

The remaining eight vaccinees who were seropositive against the three antigens before vaccination and did not participate in the nasal washings, seroconverted, No. 704 excepted.

The seroconversion results are summarized in Table III and show that the geometric mean titres postvaccination were high against the three antigens.

TABLE II

SERUM ANTIBODY TITRES IN VACCINEES
HI ANTIBODY TITRES AGAINST

| N° | A/Hong Kong/117/77 | | CNCM N° I-099 | | A/Brazil/11/78 | |
|---|---|---|---|---|---|---|
| | Pre- | Post- | Pre- | Post- | Pre- | Post- |
| | VACCINATION | | | | | |
| 490 | 5 | 160 | <5 | 160 | <10 | 160 |
| 691 | 5 | 20 | 5 | 40 | 10 | 40 |
| 694 | 20 | 80 | 10 | 40 | 10 | 40 |
| 698 | <5 | 80 | <5 | 160 | <10 | 160 |
| 703 | <5 | <5 | <5 | <5 | <10 | <10 |
| 705 | <5 | 160 | <5 | 40 | <10 | 160 |
| 707 | <5 | 40 | <5 | 40 | <10 | 160 |
| 712 | 5 | 5 | <5 | 5 | <10 | 10 |
| 713 | 10 | 320 | <5 | 320 | <10 | 160 |
| 715 | 10 | 160 | 5 | 40 | 10 | 80 |
| 689 | <5 | <5 | <5 | <5 | <10 | <10 |
| 692 | 10 | 320 | <5 | 160 | <10 | 160 |
| 693 | 10 | 320 | <5 | 160 | <10 | 160 |
| 695 | <5 | 320 | <5 | 160 | <10 | 320 |
| 662 | 40 | NT | 20 | ≧320 | 20 | 320 |

TABLE II-continued

SERUM ANTIBODY TITRES IN VACCINEES

HI ANTIBODY TITRES AGAINST

| N° | A/Hong Kong/117/77 Pre- | A/Hong Kong/117/77 Post- | CNCM N° I-099 Pre- | CNCM N° I-099 Post- | A/Brazil/11/78 Pre- | A/Brazil/11/78 Post- |
|---|---|---|---|---|---|---|
|  | VACCINATION | | | | | |
| 688 | 10 | 80 | 10 | 40 | 10 | 40 |
| 690 | 40 | 320 | 20 | 160 | 10 | ≧320 |
| 700 | 20 | 80 | 5 | 80 | 10 | 80 |
| 701 | 10 | 80 | 10 | 40 | 10 | 40 |
| 702 | 10 | 640 | 5 | 320 | 10 | ≧320 |
| 704 | 10 | 10 | 10 | 10 | 10 | 10 |
| 709 | 20 | 160 | 10 | 80 | 20 | 160 |

NT = not tested.

TABLE III

SUMMARY OF SEROCONVERSION RESULTS AGAINST A/HONG KONG/117/77, CNCM N° I-099, A/BRAZIL/11/78 AFTER ONE DOSE OF CNCM N° I-099

| Prevaccination titres | Seroconversion results A/HK/117/77 | Seroconversion results CNCM N° I-099 | Seroconversion results A/Brazil/11/78 |
|---|---|---|---|
| <5(<10 for A/Brazil/11/78) | 4/6 | 8(9)/11 | 9/11 |
| 5/10 | 9/11 | 8/9 | 8/9 |
| ≧20 | 4/4 | 2/2 | 2/2 |
| TOTAL | 17/12* | 18(19)/22** | 19/22 |
| Geometric mean titres+ (Pre- and post-vaccination) | 6/67 | 3/56 | 3/65 |

+titres <10 were counted as zero for calculation
*the sera of one vaccinee (N° 662) was not tested against A/Hong Kong/117/77
**one result is at the limit of signification (N° 712).

3. Clinical reactions

The reported symptoms were either local or present on the vaccination day. Very few severe local reactions were reported. Systemic reactions (temperature rise) were present in two volunteers but the temperature did not rise above 37.6° C.

CONCLUSION

From the above results, it can be concluded that the tested vaccine is safe and highly immunogenic and that its excretion pattern is acceptable.

We claim:

1. The recombinant influenza virus strain CNCM No. I-099.
2. A process of producing a live influenza virus vaccine which comprises growing the influenza virus strain of claim 1 in the allantoic cavity of embryonated chicken eggs for a period of time sufficient to permit production of a large amount of said virus, harvesting the resulting virus material and combining it with a pharmaceutical diluent.
3. The process according to claim 2 in which a stabilizer is added to the vaccine preparation.
4. The process according to claim 2 or 3 in which the vaccine preparation is freeze-dried prior to combining it with a pharmaceutical diluent.

* * * * *